(12) United States Patent
McCool et al.

(10) Patent No.: US 7,727,711 B2
(45) Date of Patent: Jun. 1, 2010

(54) **ANTIBODIES SPECIFIC TO ANTIGENS OF *BARTONELLA HENSELAE* AND USE OF THESE ANTIGENS IN IMMUNOASSAYS**

(75) Inventors: Tera L. McCool, Arnold, MO (US); Chien Chang Loa, Mount Laurel, NJ (US); Eli Mordechai, Robbinsville, NJ (US); Martin E. Adelson, Hillsborough, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 12/075,036

(22) Filed: Mar. 7, 2008

(65) Prior Publication Data

US 2008/0220458 A1 Sep. 11, 2008

Related U.S. Application Data

(62) Division of application No. 11/418,409, filed on May 3, 2006, now abandoned.

(60) Provisional application No. 60/684,707, filed on May 26, 2005.

(51) Int. Cl.
*C12Q 1/00* (2006.01)
*G01N 33/53* (2006.01)
*A61K 39/02* (2006.01)

(52) U.S. Cl. .................... 435/4; 424/130.1; 424/139.1; 424/141.1; 424/142.1; 424/150.1; 424/163.1; 424/164.1; 424/184.1; 424/185.1; 424/190.1; 435/7.1; 530/300; 530/350

(58) Field of Classification Search .............. 424/130.1, 424/139.1, 141.1, 142.1, 150.1, 163.1, 164.1, 424/184.1, 185.1, 190.1; 530/300, 350; 435/4, 435/7.1

See application file for complete search history.

(56) References Cited

U.S. PATENT DOCUMENTS

2003/0235876 A1* 12/2003 Bethke ...................... 435/7.32

OTHER PUBLICATIONS

Haake, D.A., et al. Heat shock response and groEL sequence of *Bartonella henselae* and *Bartonella quintana*. Microbiology, vol. 143, pp. 2807-2815, 1997.*
Sander, A., et al. Serodiagnosis of cat scratch disease: Response to *Bartonella henselae* in children and a review of diagnostic methods. Eur. J. Clin. Microbiol. Infect. Dis., vol. 20, pp. 393-401, 2001.*

* cited by examiner

*Primary Examiner*—Rodney P. Swartz
(74) *Attorney, Agent, or Firm*—Siu K. Lo, J.D.

(57) ABSTRACT

Disclosed are antibodies that bind to the antigenic proteins GroES, RpIL, GroEL, SodB, UbiG, the ABC transporter, and an expressed antigenic protein of unknown function (the "BepA" protein) of *Bartonella henselae*, and use of these antigenic proteins in immunoassays in order to determine whether a sample from a subject contains one or more of these antibodies. Presence of such an antibody in the subject indicates that the subject is or was infected with *Bartonella henselae*, or indicates that the subject has an increased likelihood of being infected presently or in the past with *Bartonella henselae*. Also disclosed are kits for performing immunoassays, wherein each kit contains one or more of these antigenic proteins and also contains the reagents necessary for conducting an immunoassay.

26 Claims, 7 Drawing Sheets

Figure 7
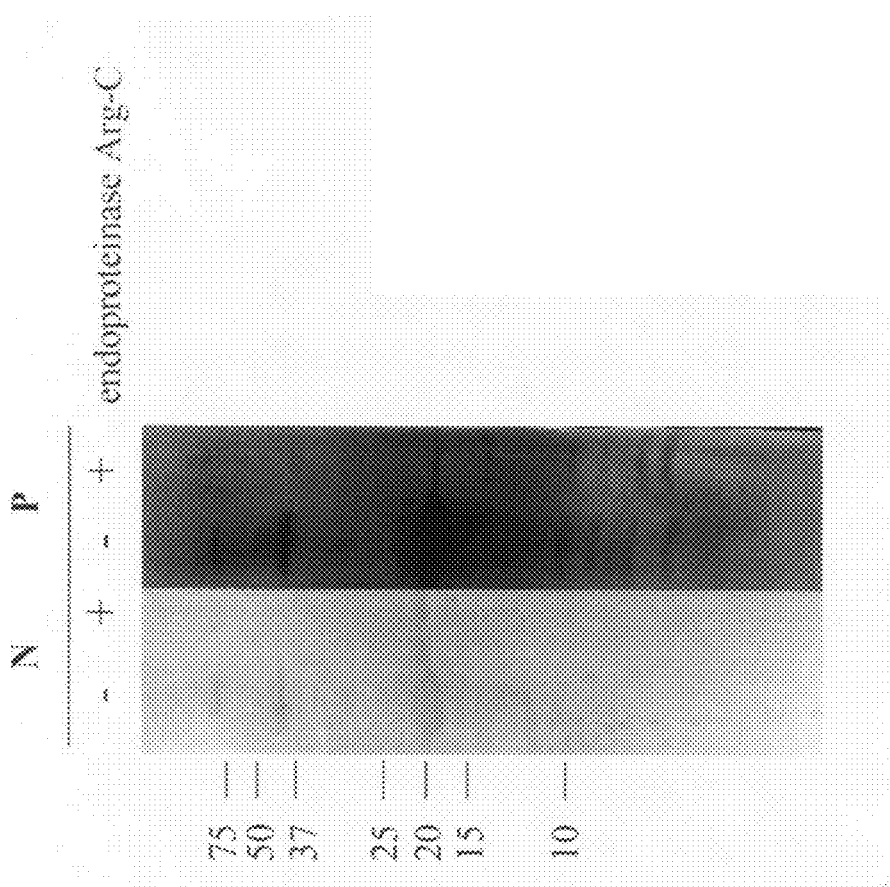
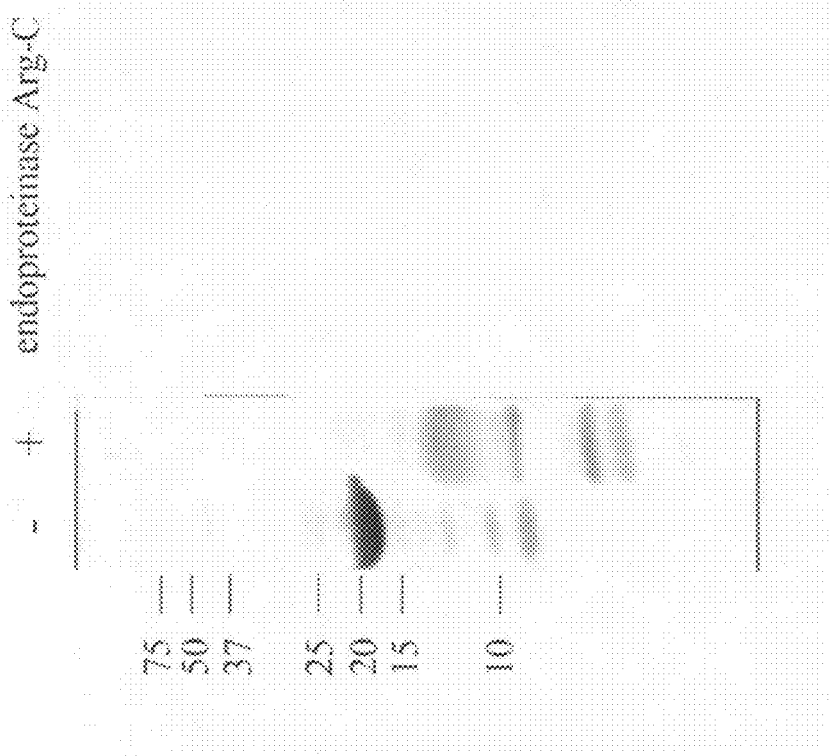

SEQUENCE LISTING

<160> NUMBER OF SEQ ID NOS: 18

<210> SEQ ID NO 1
<211> LENGTH: 39
<212> TYPE: DNA
<213> ORGANISM: Bartonella henselae

<400> SEQUENCE: 1
gacgacgaca agatggctgc taaagaagtg aagtttggc      39

<210> SEQ ID NO 2
<211> LENGTH: 35
<212> TYPE: DNA
<213> ORGANISM: Bartonella henselae

<400> SEQUENCE: 2
gaggagaagc ccggtttaga agtccatgcc gccca          35

<210> SEQ ID NO 3
<211> LENGTH: 28
<212> TYPE: DNA
<213> ORGANISM: Bartonella henselae

<400> SEQUENCE: 3
gacgacgaca agatggctaa catacaat                  28

<210> SEQ ID NO 4
<211> LENGTH: 34
<212> TYPE: DNA
<213> ORGANISM: Bartonella henselae

<400> SEQUENCE: 4
gaggagaagc ccggttaacc caaaatcccc ataa            34

<210> SEQ ID NO 5
<211> LENGTH: 35
<212> TYPE: DNA
<213> ORGANISM: Bartonella henselae

<400> SEQUENCE: 5
gacgacgaca agatgataag aaaaacagtt cccaa           35

```
<210> SEQ ID NO 6
<211> LENGTH: 33
<212> TYPE: DNA
<213> ORGANISM: Bartonella henselae

<400> SEQUENCE: 6
gaggagaagc ccggtttagc cttttagggt ttt                                    33

<210> SEQ ID NO 7
<211> LENGTH: 31
<212> TYPE: DNA
<213> ORGANISM: Bartonella henselae

<400> SEQUENCE: 7
gacgacgaca agatggctga tctagcgaag a                                      31

<210> SEQ ID NO 8
<211> LENGTH: 37
<212> TYPE: DNA
<213> ORGANISM: Bartonella henselae

<400> SEQUENCE: 8
gaggagaagc ccggtttatt taagttcaac tttagca                                37

<210> SEQ ID NO 9
<211> LENGTH: 34
<212> TYPE: DNA
<213> ORGANISM: Bartonella henselae

<400> SEQUENCE: 9
gacgacgaca agatggcttt tgaactagca cctt                                   34

<210> SEQ ID NO 10
<211> LENGTH: 36
<212> TYPE: DNA
<213> ORGANISM: Bartonella henselae

<400> SEQUENCE: 10
gaggagaagc ccggtttaaa gtccgcaatc ttcata                                 36

<210> SEQ ID NO 11
<211> LENGTH: 98
<212> TYPE: PRT
<213> ORGANISM: Bartonella henselae

<400> SEQUENCE: 11

Met Ala Asn Ile Gln Phe Arg Pro Leu His Asp Arg Val Val Arg
1               5                   10                  15

Arg Val Glu Ser Glu Asn Lys Thr Ala Gly Gly Ile Ile Pro Asp
                20                  25                  30

Thr Ala Lys Glu Lys Pro Gln Glu Gly Glu Val Ile Ala Val Gly Asn
            35                  40                  45

Gly Ala Leu Asp Asp Asn Gly Lys Arg Val Pro Leu Glu Val Lys Thr
50                  55                  60

Gly Asp Arg Ile Leu Phe Gly Lys Trp Ser Gly Thr Glu Val Lys Ile
65                  70                  75                  80

Asn Gly Glu Asp Leu Leu Ile Met Lys Glu Ser Asp Ile Met Gly Ile
                85                  90                  95

Leu Gly
```

<210> SEQ ID NO 12
<211> LENGTH: 123
<212> TYPE: PRT
<213> ORGANISM: Bartonella henselae

<400> SEQUENCE: 12

Met Ala Asp Leu Ala Lys Ile Val Glu Asp Leu Ser Asn Leu Thr Val
1               5                   10                  15

Leu Glu Ala Ala Glu Leu Ser Lys Leu Leu Glu Lys Trp Gly Val
            20                  25                  30

Ser Ala Ala Pro Val Ala Val Ala Val Ala Gly Ala Ala Ala
        35                  40                  45

Pro Val Ala Glu Glu Lys Thr Glu Phe Asp Val Ile Leu Val Glu Gly
        50                  55                  60

Gly Ala Gln Lys Ile Asn Val Ile Lys Glu Val Arg Ala Leu Thr Gly
65                  70                  75                  80

Leu Gly Leu Lys Glu Ala Lys Asp Leu Val Gly Ala Pro Lys Pro
            85                  90                  95

Ile Lys Glu Gly Ala Ser Lys Asp Glu Ala Glu Lys Ile Lys Ser Gln
            100                 105                 110

Leu Glu Ala Ala Gly Ala Lys Val Glu Leu Lys
            115                 120

<210> SEQ ID NO 13
<211> LENGTH: 174
<212> TYPE: PRT
<213> ORGANISM: Bartonella henselae

<400> SEQUENCE: 13

Met Ile Arg Lys Thr Val Pro Asn Thr Thr Phe His Thr Arg Val Arg
1               5                   10                  15

Asp Glu Ser Ile Gly Gly Asp Asn Pro Tyr Arg Trp Gln Glu Val Asn
            20                  25                  30

Ser Asp Ala Tyr Phe Lys Gly Lys Arg Val Ile Leu Phe Ser Leu Pro
        35                  40                  45

Gly Ala Phe Thr Pro Thr Cys Ser Thr Phe Gln Leu Pro Asp Phe Glu
    50                  55                  60

Lys Leu Tyr Asp Glu Phe Lys Lys Val Gly Ile Asp Glu Ile Tyr Cys
65                  70                  75                  80

Leu Ser Val Asn Asp Ala Phe Val Met Asn Ala Trp Gly Lys Ala Gln
            85                  90                  95

Gly Ile Lys Asn Val Lys Leu Ile Pro Asp Gly Ser Gly Glu Phe Thr
            100                 105                 110

Arg Lys Met Gly Met Leu Val Ala Lys Asp Asn Val Gly Phe Gly Met
        115                 120                 125

Arg Ser Trp Arg Tyr Ala Ala Val Ile Asn Asp Gly Val Ile Glu His
        130                 135                 140

Trp Phe Glu Glu Gln Gly Phe Ser Asp Asn Cys Ala Thr Asp Pro Tyr
145                 150                 155                 160

Glu Val Ser Ser Pro Gln Asn Val Leu Lys Thr Leu Lys Gly
            165                 170

<210> SEQ ID NO 14
<211> LENGTH: 547
<212> TYPE: PRT
<213> ORGANISM: Bartonella henselae

<400> SEQUENCE: 14

```
Met Ala Ala Lys Glu Val Lys Phe Gly Arg Glu Ala Arg Glu Arg Leu
1               5                   10                  15

Leu Arg Gly Val Asp Ile Leu Ala Asn Ala Val Lys Val Thr Leu Gly
            20                  25                  30

Pro Lys Gly Arg Asn Val Val Ile Asp Lys Ser Phe Gly Ala Pro Arg
        35                  40                  45

Ile Thr Lys Asp Gly Val Ser Val Ala Lys Glu Ile Glu Leu Glu Asp
    50                  55                  60

Lys Phe Glu Asn Met Gly Ala Gln Met Leu Arg Glu Val Ala Ser Lys
65                  70                  75                  80

Thr Asn Asp Ile Ala Gly Asp Gly Thr Thr Thr Ala Thr Val Leu Gly
                85                  90                  95

Gln Ala Ile Val Gln Glu Gly Val Lys Ala Val Ala Ala Gly Met Asn
            100                 105                 110

Pro Met Asp Leu Lys Arg Gly Ile Asp Ala Ala Val Asp Glu Val Val
        115                 120                 125

Ala Asn Leu Phe Lys Lys Ala Lys Lys Ile Gln Thr Ser Ala Glu Ile
130                 135                 140

Ala Gln Val Gly Thr Ile Ser Ala Asn Gly Ala Ala Glu Ile Gly Lys
145                 150                 155                 160

Met Ile Ala Asp Ala Met Glu Lys Val Gly Asn Glu Gly Val Ile Thr
                165                 170                 175

Val Glu Glu Ala Lys Thr Ala Glu Thr Glu Leu Glu Val Val Glu Gly
            180                 185                 190

Met Gln Phe Asp Arg Gly Tyr Leu Ser Pro Tyr Phe Val Thr Asn Ala
        195                 200                 205

Glu Lys Met Val Ala Asp Leu Asp Asp Pro Tyr Ile Leu Ile His Glu
    210                 215                 220

Lys Lys Leu Ser Asn Leu Gln Ser Leu Leu Pro Val Leu Glu Ala Val
225                 230                 235                 240

Val Gln Ser Gly Lys Pro Leu Leu Ile Ile Ala Glu Asp Val Glu Gly
                245                 250                 255

Glu Ala Leu Ala Thr Leu Val Val Asn Lys Leu Arg Gly Gly Leu Lys
            260                 265                 270

Ile Ala Ala Val Lys Ala Pro Gly Phe Gly Asp Arg Arg Lys Ala Met
        275                 280                 285

Leu Glu Asp Ile Ala Ile Leu Thr Ser Gly Gln Val Ile Ser Glu Asp
    290                 295                 300

Val Gly Ile Lys Leu Glu Asn Val Thr Leu Asp Met Leu Gly Arg Ala
305                 310                 315                 320

Lys Lys Val Asn Ile Ser Lys Glu Asn Thr Thr Ile Ile Asp Gly Ala
                325                 330                 335

Gly Gln Lys Ser Glu Ile Asn Ala Arg Val Asn Gln Ile Lys Val Gln
            340                 345                 350

Ile Glu Glu Thr Thr Ser Asp Tyr Asp Arg Glu Lys Leu Gln Glu Arg
        355                 360                 365

Leu Ala Lys Leu Ala Gly Gly Val Ala Val Ile Arg Val Gly Gly Ala
    370                 375                 380

Thr Glu Val Glu Val Lys Glu Lys Lys Asp Arg Val Asp Asp Ala Leu
385                 390                 395                 400

Asn Ala Thr Arg Ala Ala Val Glu Glu Gly Ile Val Ala Gly Gly Gly
                405                 410                 415
```

```
Thr Ala Leu Leu Arg Ala Ala Asn Ala Leu Thr Val Lys Gly Ser Asn
            420                 425                 430

Pro Asp Gln Glu Ala Gly Ile Asn Ile Val Arg Arg Ala Leu Gln Ala
            435                 440                 445

Pro Ala Arg Gln Ile Ala Thr Asn Ala Gly Glu Glu Ala Ala Ile Ile
            450                 455                 460

Val Gly Lys Val Leu Glu Asn Asn Ala Asp Thr Phe Gly Tyr Asn Thr
465                 470                 475                 480

Ala Thr Gly Glu Phe Gly Asp Leu Ile Ala Leu Gly Ile Val Asp Pro
                485                 490                 495

Val Lys Val Val Arg Ser Ala Leu Gln Asn Ala Ala Ser Ile Ala Ser
            500                 505                 510

Leu Leu Ile Thr Thr Glu Ala Met Val Ala Glu Val Pro Lys Lys Asp
            515                 520                 525

Thr Pro Val Pro Pro Met Pro Gly Gly Met Gly Gly Met Gly Gly
            530                 535                 540

Met Asp Phe
545

<210> SEQ ID NO 15
<211> LENGTH: 200
<212> TYPE: PRT
<213> ORGANISM: Bartonella henselae

<400> SEQUENCE: 15

Met Ala Phe Glu Leu Ala Pro Leu Pro Tyr Asp Tyr Asp Ser Leu Ser
1               5                   10                  15

Pro Tyr Met Ser Arg Glu Thr Leu Glu Tyr His His Asp Lys His His
            20                  25                  30

Leu Ala Tyr Leu Thr Asn Thr Asn Phe Val Lys Asp Leu Gly Leu
            35                  40                  45

Glu Asn Glu Ser Leu Glu Asn Ile Val Lys Lys Ser Phe Gly Gln Asn
50                  55                  60

Ile Gly Leu Phe Asn Asn Ala Ala Gln Tyr Tyr Asn His Asn His Phe
65                  70                  75                  80

Trp His Trp Met Lys Lys Gly Gly Gly Gln Lys Leu Pro Glu Lys
                85                  90                  95

Leu Ala Lys Ala Ile Glu Ser Asp Leu Gly Gly Tyr Asp Lys Phe Arg
            100                 105                 110

Ala Asp Phe Ile Ala Thr Ala Ile Ala Gln Phe Gly Ser Gly Trp Ala
            115                 120                 125

Trp Ile Ala Val Lys Asp Gly Lys Leu Glu Ile Met Lys Thr Pro Asn
            130                 135                 140

Gly Glu Asn Pro Leu Val His Asn Ala Gln Pro Ile Leu Gly Val Asp
145                 150                 155                 160

Val Trp Glu His Ser Tyr Tyr Ile Asp Tyr Arg Asn Val Arg Pro Lys
                165                 170                 175

Tyr Leu Glu Ala Phe Val Asp His Leu Ile Asn Trp Asp Tyr Val Leu
            180                 185                 190

Lys Leu Tyr Glu Asp Cys Gly Leu
            195                 200

<210> SEQ ID NO 16
<211> LENGTH: 247
<212> TYPE: PRT
```

-continued

```
<213> ORGANISM: Bartonella henselae

<400> SEQUENCE: 16

Met Ile Asn Glu Thr Arg Thr Thr Leu Asp Gln Ser Glu Val Asp His
1               5                   10                  15

Phe Ser Arg Ile Ala Ala Glu Trp Trp Asn Pro His Gly Lys Phe Arg
            20                  25                  30

Pro Leu His Gln Phe Asn Pro Thr Arg Leu Ala Tyr Ile Arg Glu Lys
        35                  40                  45

Ile Cys Leu Glu Leu His Arg Asp Pro Val Ser Leu Lys Pro Phe Glu
    50                  55                  60

Asn Leu Lys Ile Leu Asp Ile Gly Cys Gly Gly Gly Leu Leu Cys Glu
65                  70                  75                  80

Pro Met Ala Arg Leu Gly Ala Met Val Val Gly Ala Asp Ala Ser Gln
                85                  90                  95

Thr Asn Ile Glu Val Ala Lys Ile His Ala Ala Gln Asn Gly Leu Ser
            100                 105                 110

Ile Asp Tyr Arg Thr Thr Thr Ala Glu Ala Leu Ala Thr Glu Gly Glu
        115                 120                 125

Gln Phe Asp Ile Ile Leu Asn Met Glu Val Val Glu His Val Ala Asp
    130                 135                 140

Val Asn Leu Phe Ile Glu Ala Thr Ala Lys Met Leu Lys Pro Gln Gly
145                 150                 155                 160

Leu Met Phe Ile Ser Thr Leu Asn Arg Thr Trp Lys Ala Trp Gly Leu
                165                 170                 175

Ala Ile Ile Gly Ala Glu Tyr Ile Leu Arg Trp Leu Pro Lys Gly Thr
            180                 185                 190

His Asn Tyr Lys Lys Phe Leu Lys Pro Arg Glu Leu Lys Asn Leu Leu
        195                 200                 205

Leu Gln Asn Ala Leu Thr Val Val Asp Glu Ile Gly Val Thr Tyr Asn
    210                 215                 220

Pro Leu Asn Asp Ser Trp Asn Arg Ser Lys Asp Met Asn Val Asn Tyr
225                 230                 235                 240

Leu Leu Leu Ala Lys Lys Ser
                245

<210> SEQ ID NO 17
<211> LENGTH: 250
<212> TYPE: PRT
<213> ORGANISM: Bartonella henselae

<400> SEQUENCE: 17

Met Lys Leu Leu Ala Val Ala Leu Ile Thr Asn Leu Val Leu Phe Thr
1               5                   10                  15

Gln Leu Ala Asn Ala Lys Thr Leu Lys Ile Ala Ser Asp Ala Ser Tyr
            20                  25                  30

Pro Pro Phe Ser Tyr Val Asn Ser Asn Asn Glu Leu Gln Gly Phe Asp
        35                  40                  45

Ile Asp Ile Ser Tyr Ala Leu Cys Lys Lys Met Asn Val Glu Cys Thr
    50                  55                  60

Ile Val Thr Gln Asp Phe Glu Gly Met Ile Pro Gly Leu Leu Ala Lys
65                  70                  75                  80

Lys Tyr Asp Ala Ile Ile Ser Ser Leu Ala Pro Thr Glu Glu Arg Leu
                85                  90                  95

Gln Lys Ile Asp Phe Thr Asp Ala Tyr Tyr Ser Thr Glu Leu Val Val
```

```
                    100                 105                 110
Ile Val His Lys Asp Ser Gly Ile Lys Glu Ile Ser Ala Glu Ala Phe
            115                 120                 125

Lys Asp Lys Asn Leu Gly Val Gln Ser Asn Thr Thr Gln Ala Val Tyr
            130                 135             140

Ala Glu Asp His Tyr Ala Ala Glu Gly Val Asn Ile Lys Leu Tyr Pro
145                 150                 155                 160

Thr Ala Ile Glu Val Lys Arg Asp Leu Leu Ser His Arg Leu Asp Ile
                165                 170                 175

Val Ile Ser Asp Lys Leu Ala Ala Val Asn Trp Leu Glu Asn Glu Glu
            180                 185                 190

Lys Asp Cys Cys Gln Leu Leu Gly Ser Leu Lys Lys Thr Lys Leu Pro
            195                 200                 205

Ile Ala Ile Ala Ile Arg Lys Asn Asn Asn Asp Leu Lys Asn Lys Phe
            210                 215                 220

Asn Glu Ala Ile Lys Glu Ile Arg Glu Asp Gly Thr Tyr Asp Lys Ile
225                 230                 235                 240

Met Lys Lys Tyr Phe Thr Phe Asp Ile Tyr
                245                 250

<210> SEQ ID NO 18
<211> LENGTH: 91
<212> TYPE: PRT
<213> ORGANISM: Bartonella henselae

<400> SEQUENCE: 18

Lys Trp Gly Val Ser Ala Ala Pro Val Ala Val Ala Ala Val Ala
1               5                   10                  15

Gly Ala Ala Pro Val Ala Glu Glu Lys Thr Glu Phe Asp Val Ile
            20                  25                  30

Leu Val Glu Gly Gly Ala Gln Lys Ile Asn Val Ile Lys Glu Val Arg
            35                  40                  45

Ala Leu Thr Gly Leu Gly Leu Lys Glu Ala Lys Asp Leu Val Glu Gly
        50                  55                  60

Ala Pro Lys Pro Ile Lys Glu Gly Ala Ser Lys Asp Glu Ala Glu Lys
65                  70                  75                  80

Ile Lys Ser Gln Leu Glu Ala Ala Gly Ala Lys
                85                  90
```

ANTIBODIES SPECIFIC TO ANTIGENS OF *BARTONELLA HENSELAE* AND USE OF THESE ANTIGENS IN IMMUNOASSAYS

CROSS REFERENCES TO RELATED APPLICATIONS

The present application is a divisional of U.S. Ser. No. 11/418,409, filed May 3, 2006 (now abandoned); which claims the benefit under 35 U.S.C. § 119(e) of U.S. Provisional Application No. 60/684,707, filed May 26, 2005. The entire contents of each of the above-referenced patent applications are hereby expressly incorporated herein by reference.

BACKGROUND OF THE INVENTION

1. Field of the Invention

The present invention is broadly concerned with antibodies specific to antigens of *Bartonella henselae* and use of these antigens in immunoassays. More particularly, the present invention relates to antibodies specific to the GroES protein, the RpIL protein, an expressed protein of unknown function (the "BepA" protein), the GroEL protein, the SodB protein, the UbiG protein, and the ABC transporter protein of *Bartonella henselae*, and use of these antigenic proteins in immunoassays in order to determine whether a patient is or was infected with *Bartonella henselae*.

2. Description of the Related Art

Epidemiological, serological, and molecular studies have implicated *Bartonella henselae* as the primary causative agent of Cat Scratch Disease (CSD), a frequent self-limiting zoonotic condition which is transferred from cat scratches or bites to people (Bergmans, A. M., J. W. Groothedde, J. F. Schellekens, J. D. van Embden, J. M. Ossewaarde, and L. M. Schouls. 1995. Etiology of cat scratch disease: comparison of polymerase chain reaction detection of *Bartonella* (formerly *Rochalimaea*) and *Afipia felis* DNA with serology and skin tests. J. Infect. Dis. 171:916-23.). Development of CSD is common with a reported incidence rate of 0.77 to 0.86 cases per 100,000 people.

In the United States, approximately 22,000 people develop CSD annually (Koehler, J. E., C. A. Glaser, and J. W. Tappero. 1994. *Rochalimaea henselae* infection. A new zoonosis with the domestic cat as reservoir. JAMA 271:531-5; Peter, J. B., M. Boyle, M. Patnaik, T. L. Hadfield, N. E. Barka, W. A. Schwartzman, and R. S. Penny. 1994. Persistent generalized lymphadenopathy and non-Hodgkin's lymphoma in AIDS: association with *Rochalimaea henselae* infection. Clin. Diagn. Lab. Immunol. 1:115-6.). Approximately 11% of CSD cases are atypical and symptoms can include granulomatous conjunctivitis, oculoglandular syndrome, tonsillitis, visceral granulomatous disease, encephalitis, and cerebral arteritis (Schwartzman, W. A. 1992. Infections due to Rochalimaea: the expanding clinical spectrum. Clin. Infect. Dis. 15:893-900.).

Cats serve as a major reservoir of *Bartonella henselae*. Pathogen analyses of domesticated cats in the United States have estimated that approximately 28% are chronically infected with *Bartonella henselae* with no obvious clinical symptoms (Kordick, D. L., K. H. Wilson, D. J. Sexton, T. L. Hadfield, H. A. Berkhoff, and E. B. Breitschwerdt. 1995. Prolonged *Bartonella* bacteremia in cats associated with cat-scratch disease patients. J. Clin. Microbiol. 33:3245-51.).

Infection with *Bartonella henselae* in significant cases can result in bacillary angiomatitis or endocarditis. Children and immunocompromised individuals are especially vulnerable to this bacterium. In immunocompromised patients, including those who have been infected with HIV-1 and have developed AIDS, infection with *Bartonella henselae* can result in bacillary angiomatosis or peliosis hepatis and may also include visceral involvement (Fournier, P. E., and D. Raoult. 1998. Cat scratch disease and an overview of other *Bartonella henselae* related infections, p. 32-62. In A. Schmidt (ed.), *Bartonella* and *Afipia* species emphasizing *Bartonella henselae*. Karger, Basel, Switzerland.). The U.S. Public Health Service and the Infectious Diseases Society of America has recognized the risk of contracting Bartonellosis, especially in immunocompromised HIV-1 infected individuals, and have published suggested guidelines for cat ownership as feline-to-human transmission of *Bartonella henselae* is the most commonly recognized route (Kaplan, J. E., H. Masur, and K. K. Holmes. 2002. Guidelines for preventing opportunistic infections among HIV-infected persons—2002. Recommendations of the U.S. Public Health Service and the Infectious Diseases Society of America. MMWR Recomm. Rep. 51:1-52.).

*Bartonella* spp. also have been found in 39% of deer ticks (species: *Ixodes scapularis*) (Adelson, M. E., R. S. Rao, R. C. Tilton, K. Cabets, E. Eskow, L. Fein, J. C. Occi, and E. Mordechai. 2004. Prevalence of *Borrelia burgdorferi*, *Bartonella* spp., *Babesia microti*, and *Anaplasm phagocytophila* in *Ixodes scapularis* ticks collected in Northern New Jersey. J. Clin. Microbiol. 42:2799-801.). This information, in conjunction with a clinical case study in which patients were co-infected with *Borrelia burgdorferi*, the causative agent of Lyme Disease, and *Bartonella henselae*, suggests that tick bites may serve as an additional method of *Bartonella henselae* transmission (Eskow, E., R. V. Rao, and E. Mordechai. 2001. Concurrent infection of the central nervous system by *Borrelia burgdorferi* and *Bartonella henselae*: evidence for a novel tick-borne disease complex. Arch. Neurol. 58:1357-63.).

Current clinical diagnostics rely on culturing, immunofluorescence assay ("IFA"), and polymerase chain reaction ("PCR") technologies. The culturing of *Bartonella* from blood samples is technically challenging and is a low-yield procedure. Recommended growth conditions include lengthy incubation periods of at least twenty-one days on Columbia blood agar plates (Raoult, D., and R. Tilton. 1999. Dictionary of Infectious Diseases. Elsevier Publishing, New York.; Spach, D. H., and J. E. Koehler. 1998. *Bartonella*-associated infections. Infect. Dis. Clin. North. Am. 12:137-55.). Culturing of *Bartonella* is therefore not considered an effective and reproducible diagnostic procedure to detect *Bartonella* spp. infections.

*Bartonella henselae* IFAs have high sensitivity and specificity. However, cross-reactivity with other human pathogens, including *Coxiella burnetii*, *Chlamydia* spp., *Rickettsia rickettsii*, *Ehrlichia chaffeensis*, *Treponema pallidum*, *Francisella tularensis*, and *Mycoplasma pneumoniae* has been reported (Cooper, M. D., M. R. Hollingdale, J. W. Vinson, and J. Costa. 1976. A passive hemagglutination test for diagnosis of trench fever due to *Rochalimaea quintana*. J. Infect. Dis. 134:605-9.; Drancourt, M., J. L. Mainardi, P. Brouqui, F. Vandenesch, A. Carta, F. Lehnert, J. Etienne, F. Goldstein, J. Acar, and D. Raoult. 1995. *Bartonella* (*Rochalimaea*) *quintana* endocarditis in three homeless men. N. Engl. J. Med. 332:419-23.; McGill, S. L., R. L. Regnery, and K. L. Karem. 1998. Characterization of human immunoglobulin (Ig) isotype and IgG subclass response to *Bartonella henselae* infection. Infect. Immun. 66:5915-20.). In addition, IFAs rely heavily on technicians for the determination of test results which introduces subjectivity into the interpretation of these test results, are time-consuming to score, and require expensive fluorescent microscopes.

Bartonella PCR amplifies the 16S rRNA gene which permits the simultaneous detection of DNA from *Bartonella henselae*, *Bartonella quintana*, *Bartonella bacilliformis*, *Bartonella elizabethae*, and *Bartonella clarridgeiae* (Bergmans, A. M., J. W. Groothedde, J. F. Schellekens, J. D. van Embden, J. M. Ossewaarde, and L. M. Schouls. 1995. Etiology of cat scratch disease: comparison of polymerase chain reaction detection of *Bartonella* (formerly *Rochalimaea*) and *Afipia felis* DNA with serology and skin tests. J. Infect. Dis. 171:916-23.). While allowing for species-specific identification, PCR requires the presence of *Bartonella* organisms or DNA in the tested sample.

The antibody response to *Bartonella henselae* has been studied in several different types of mammals; however, in order to develop sensitive and accurate serological assays, for example, the human antibody response to *Bartonella henselae* needs to be elucidated in detail. Identification of antigenic proteins, particularly, is of paramount importance to the creation of improved clinical diagnostics.

BRIEF SUMMARY OF THE INVENTION

The present invention provides the antigenic proteins noted in the preceding paragraph, wherein these proteins are useful, for example, in immunoassays capable of detecting antibodies specific to *Bartonella henselae*.

More specifically, the present invention is directed to an isolated antibody capable of binding to an antigen, wherein the antigen consists of the amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18. In an embodiment, the antibody is human. In another embodiment, the antibody is polyclonal.

The present invention also is drawn to a kit containing (a) an isolated antigen comprising the amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18 and (b) the reagents necessary for conducting an immunoassay, wherein the immunoassay is capable of detecting the presence of an antibody in a sample, wherein the antibody is capable of binding to an antigen consisting of the amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18. In an embodiment, the immunoassay is an IFA. In another embodiment, the immunoassay is an enzyme-linked immunosorbent assay ("ELISA"). In yet another embodiment, the isolated antigen in (a) consists of the amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18

The present invention also relates to a method for determining whether a subject contains an antibody capable of binding to an antigen consisting of the amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18 comprising (a) conducting an immunoassay on a sample from the subject, and (b) determining that the subject contains the antibody if the results of the immunoassay indicate that the antibody is present in the sample, or determining that the subject does not contain the antibody if the results of the immunoassay indicate that the antibody is not present in the sample. In an embodiment, the subject is human. In another embodiment, the immunoassay is an IFA. In yet another embodiment, the immunoassay is an ELISA.

The present invention also pertains to a method for determining whether a subject has an increased likelihood of being infected presently or in the past with *Bartonella henselae* comprising (a) conducting an immunoassay on a sample from the subject, and (b) determining that the subject has an increased likelihood of being infected presently or in the past with *Bartonella henselae* if the results of the immunoassay indicate that an antibody is present in the sample, or determining that the subject does not have an increased likelihood of being infected presently or in the past with *Bartonella henselae* if the results of the immunoassay indicate that the antibody is not present in the sample, wherein the antibody is capable of binding to an antigen consisting of the amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18. In an embodiment, the subject is human. In another embodiment, the immunoassay is an IFA. In yet another embodiment, the immunoassay is an ELISA.

The present invention also is drawn to a method for determining whether a subject has a present infection with *Bartonella henselae* or had a past infection with *Bartonella henselae* comprising (a) conducting an immunoassay on a sample from the subject, and (b) determining that the subject has a present infection with *Bartonella henselae* or had a past infection with *Bartonella henselae* if the results of the immunoassay indicate that an antibody is present in the sample, or determining that the subject does not have a present infection with *Bartonella henselae* or did not have a past infection with *Bartonella henselae* if the results of the immunoassay indicate that the antibody is not present in the sample, wherein the antibody is capable of binding to an antigen consisting of the amino acid sequence of SEQ ID NO:11, SEQ ID NO:12, SEQ ID NO:13, SEQ ID NO:14, SEQ ID NO:15, SEQ ID NO:16, SEQ ID NO:17, or SEQ ID NO:18. In an embodiment, the subject is human. In another embodiment, the immunoassay is an IFA. In yet another embodiment, the immunoassay is an ELISA.

BRIEF DESCRIPTION OF THE DRAWINGS

FIG. 7 illustrates a reactive epitope of RpIL. Recombinant RpIL was digested overnight with endoproteinase Arg-C. rRpIL that had not undergone digestion (−) and rRpIL that had (+) were loaded in equal amounts onto a 16.5% Tris-Tricine gel (A). After transfer, membranes were exposed to either patient sera (P) or normal sera (N). Bound antibodies were detected with anti-human IgG-HRP (B). Blots shown are representative.

DETAILED DESCRIPTION

Figure 1:
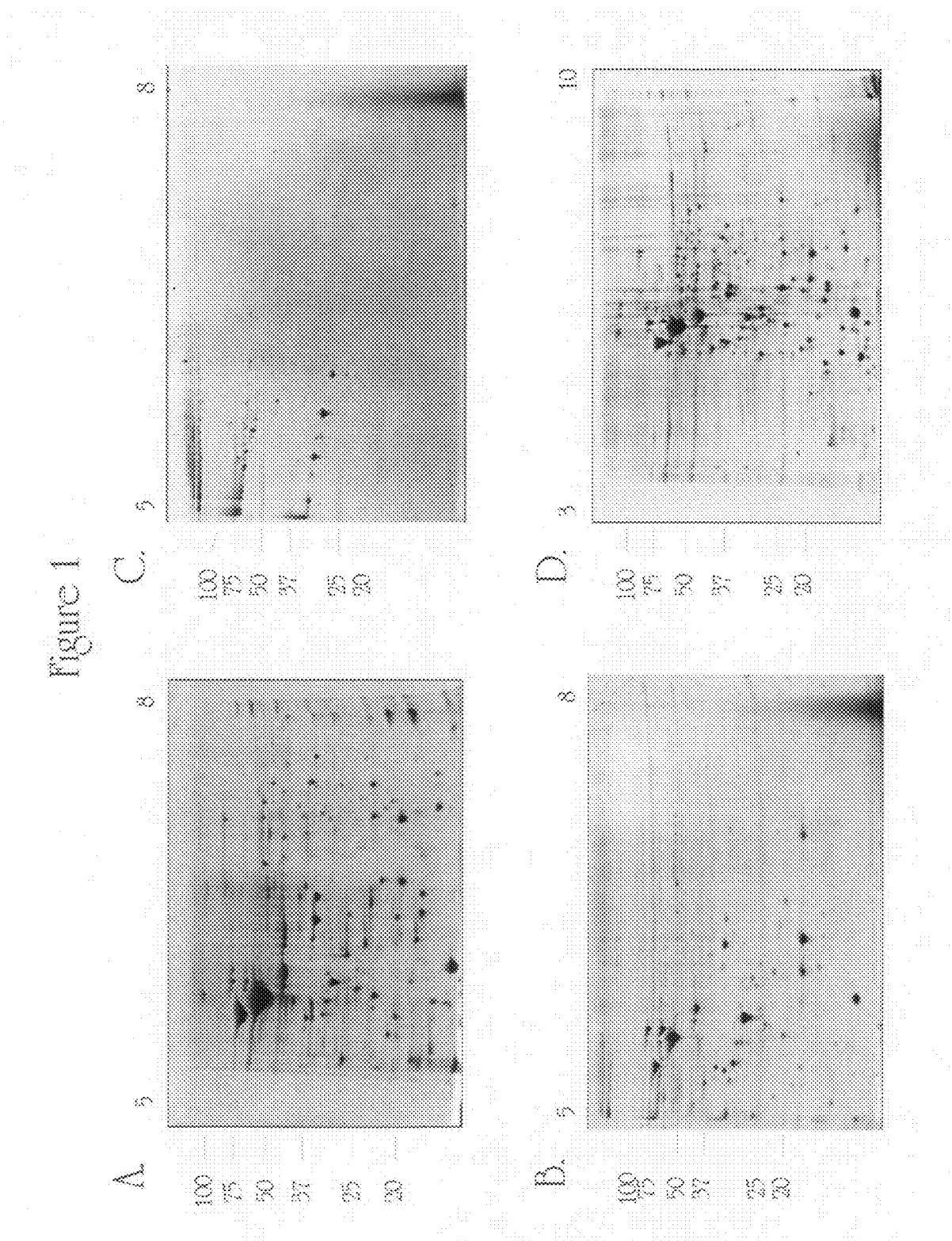
FIG. 1 illustrates a two-dimensional analysis of proteins of *Bartonella henselae*. Soluble (A), less soluble (B), and insoluble (C) proteins derived from *Bartonella henselae* were separated based on isoelectric point (pI 5-8) and molecular weight. Gels were stained with Coomassie Blue. The soluble fractions were also separated using a larger pI range (3-10) (D) to visualize the majority of proteins found in *Bartonella henselae*.

The following examples illustrate the discovery that the GroES protein, the RpIL protein, the BepA protein, the GroEL protein, the SodB protein, the UbiG protein, and the ABC transporter protein produced by *Bartonella henselae* are each antigenic. Each of these antigens can be used in an immunoassay to determine whether a subject possesses an antibody that binds to it. These examples are set forth by way of illustration only, and nothing therein shall be taken as a limitation upon the overall scope of the invention.

Techniques applicable to the present invention are described in Short Protocols in Molecular Biology, 5$^{th}$ edition, Volumes 1 and 2, 2002, Edited by Frederick M. Ausubel et al., John Wiley & Sons, Inc., Hoboken, N.J., the entire contents of which are hereby incorporated by reference; Short Protocols in Molecular Biology, 3$^{rd}$ edition, 1997, Edited by Frederick M. Ausubel et al., John Wiley & Sons, Inc., New York, N.Y., the entire contents of which are hereby incorporated by reference; Short Protocols in Immunology, 2005, Edited by John E. Coligan et al., John Wiley & Sons, Hoboken, N.J., the entire contents of which are hereby incorporated by reference; and The Immunoassay Handbook, 3$^{rd}$ Edition, 2005, Edited by David Wild, Elsevier, Amsterdam, San Diego, Calif., Oxford, the entire contents of which are hereby incorporated by reference.

EXAMPLE 1

*Bartonella henselae* Proteome

*Bartonella henselae* proteins were isolated from cultures of *Bartonella henselae* Houston-1. *Bartonella henselae* was grown to an optical density of 0.3 in 200 ml of BBH-H media at 37° C., shaking at 180 rpm, for five days (Chenoweth, M. R., G. A. Somerville, D. C. Krause, K. L. O'Reilly, and F. C. Gherardini. 2004. Growth characteristics of *Bartonella henselae* in a novel liquid medium: primary isolation, growth-phase-dependent phage induction, and metabolic studies. Appl. Environ. Microbiol. 70:656-63.). The presence of *Bartonella henselae* in the culture was verified by an in-house PCR developed against the *Bartonella henselae* 16S rRNA. Culture pellets obtained by centrifugation were resuspended in PBS and sonicated. The soluble fraction was desalted using a desalting kit (BioRad, Hercules, Calif.) and resuspended in 8 M urea, 2% CHAPS, 40 mM DTT, 0.2% Bio-Lyte 3/10 ampholyte. The protein concentration was determined by a reducing agent-compatible detergent-compatible ("RC DC") assay (BioRad, Hercules, Calif.).

Three different protein fractions were obtained based on protein solubilities. Fraction 1 contained proteins with the highest solubility and 2-3 times the amount of protein isolated in fraction 2, which contained proteins of intermediate solubility. Fraction 3 contained proteins less soluble than those in fraction 2 and yielded 2-3 times less protein than that isolated in fraction 2.

Proteins from each fraction were separated by two-dimensional electrophoresis. 180 μg of protein were loaded onto pH 3-10 immobilized pH gradient ("IPG") strips (BioRad, Hercules, Calif.) during overnight passive gel rehydration. Isoelectric Focusing ("IEF") was performed under standard conditions. Focused IEF strips were equilibrated for 15 minutes in 6 M urea, 2% SDS, 0.05 M Tris/HCl, 20% glycerol, 2% DTT and then 15 minutes in 6 M urea, 2% SDS, 0.05 M Tris/HCl, 20% glycerol, 2.5% iodoacetamide and then overlayed onto a 8-15% gradient SDS-PAGE gel (BioRad, Hercules, Calif.). The gels were run for 65 minutes at 200V.

Separations utilized a narrow pH range (5-8) and demonstrated a decrease in the number of proteins concomitant with a decrease in solubility. Computer analysis using PDQuest™ (BioRad, Hercules, Calif.) identified over 900 protein spots in fraction 1, 358 spots in fraction 2, and 138 spots in fraction 3 (FIG. 1A-C). Fraction 1 required minimal processing and smaller amounts of *Bartonella henselae* culture to prepare and still yielded a significant number of spots. Hence, fraction 1 was pursued further in these studies. Use of IPG strips with a pH 3-10 resulted in an increase in the number of proteins observed in fraction 1 to more than 1000 spots (FIG. 1D).

Spots of interest were excised from Coomassie-Blue stained gels and sent for Matrix Assisted Laser Desorption Ionization Mass Spectrometry "MALDI-MS" peptide fingerprinting. This resulted in identification of proteins of interest. The genes encoding these proteins were subsequently amplified from *Bartonella henselae* DNA and ligated into a pET30 Ek/LIC expression vector (EMD Biosciences, San Diego, Calif.) (Table 1). Protein expression by transformed DH5α cells was induced using the Overnight Express™ AutoInduction System (EMD Biosciences, San Diego, Calif.). Proteins were purified by two passages over a nickel-nitrilotriacetic acid ("Ni-NTA") resin column (EMD Biosciences, San Diego, Calif.). After completion of buffer exchange into PBS, the proteins were concentrated. Final protein concentrations were determined by bicinchoninic acid ("BCA") assay.

TABLE 1

Primers used for cloning of *Bartonella henselae* genetic material into the pET30EK/LIC vector.

| Protein | Forward Primer | Reverse Primer |
|---------|----------------|----------------|
| GroEL | 5'-GACGACGACAAGATGGCT-GCTAAAGAAGTGAAGTTTGGC-3' (SEQ ID NO: 1) | 5'-GAGGAGAAGCCCGGTTTAGA-AGTCCATGCCGCCCA-3' (SEQ ID NO: 2) |
| GroES | 5'-GACGACGACAAGATGGCTAA-CATACAAT-3' (SEQ ID NO: 3) | 5'-GAGGAGAAGCCCGGTTAACC-CAAAATCCCCATAA-3' (SEQ ID NO: 4) |
| BepA | 5'-GACGACGACAAGATGATAAG-AAAAACAGTTCCCAA-3' (SEQ ID NO: 5) | 5'-GAGGAGAAGCCCGGTTTAGC-CTTTTAGGGTTTT-3' (SEQ ID NO: 6) |
| RpIL | 5'-GACGACGACAAGATGGCTGA-TCTAGCGAAGA-3' (SEQ ID NO: 7) | 5'-GAGGAGAAGCCCGGTTTATT-TAAGTTCAACTTTAGCA-3' (SEQ ID NO: 8) |
| SodB | 5'-GACGACGACAAGATGGCTTT-TGAACTAGCACCTT-3' (SEQ ID NO: 9) | 5'-GAGGAGAAGCCCGGTTTAAA-GTCCGCAATCTTCATA-3' (SEQ ID NO: 10) |

EXAMPLE 2

Reactivity of Patient Sera to *Bartonella henselae* Soluble Proteins

In order to determine which *Bartonella henselae* proteins can bind to antibodies, Western blots were performed using a two-dimensional map of fraction 1 using patient and normal human sera. *Bartonella henselae* IFA positive and negative human serum samples were purchased from Dr. D. Raoult (Université de la Méditerranée, France) and from Focus Diagnostics (Cypress, Calif.). Serum samples with *Bartonella henselae* IFA titers ≧1:64 were considered positive sera, samples with IFA titers<1:64 were considered negative sera. All serum samples were verified in-house by IFA (Focus Diagnostics, Cypress, Calif.) prior to use.

Western blotting was performed using a standard protocol. Briefly, proteins were electrophoretically transferred from SDS-PAGE gels onto polyvinyladine difluoride ("PVDF") membranes. Transfer was performed at 100V for 60 minutes. After transfer, the membranes were stained with RedAlert™ (EMD Biosciences, San Diego, Calif.). The membranes were washed in PBS-Tween 20 and exposed to a 1:500 dilution of either normal or patient sera diluted in 1% bovine serum albumin (BSA)-PBS-Tween 20 for one hour. After washing of the membrane, anti-human IgG-HRP (KPL, Gaithersburg, Md.) was added at a dilution of 1:2000 in 1% BSA-PBS-Tween 20. 0.5 mg/ml 3,3'-diaminobenzidine (DAB; Sigma, St. Louis, Mo.) was then added. After exposure to substrate, the blots were imaged and analyzed by the software package PDQuest™.

Figure 2:
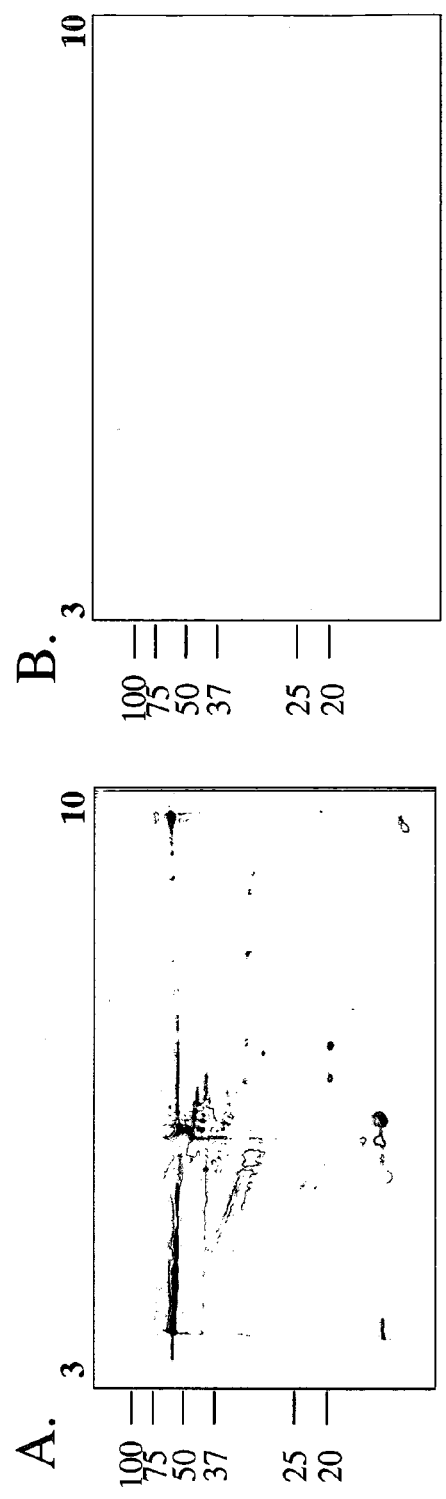
FIG. 2 illustrates the reactivity of patient serum (A) and normal serum (B) to the soluble fraction of *Bartonella henselae*. Western blots shown are representative blots of fourteen patient sera and seven normal sera.
Figure 3:
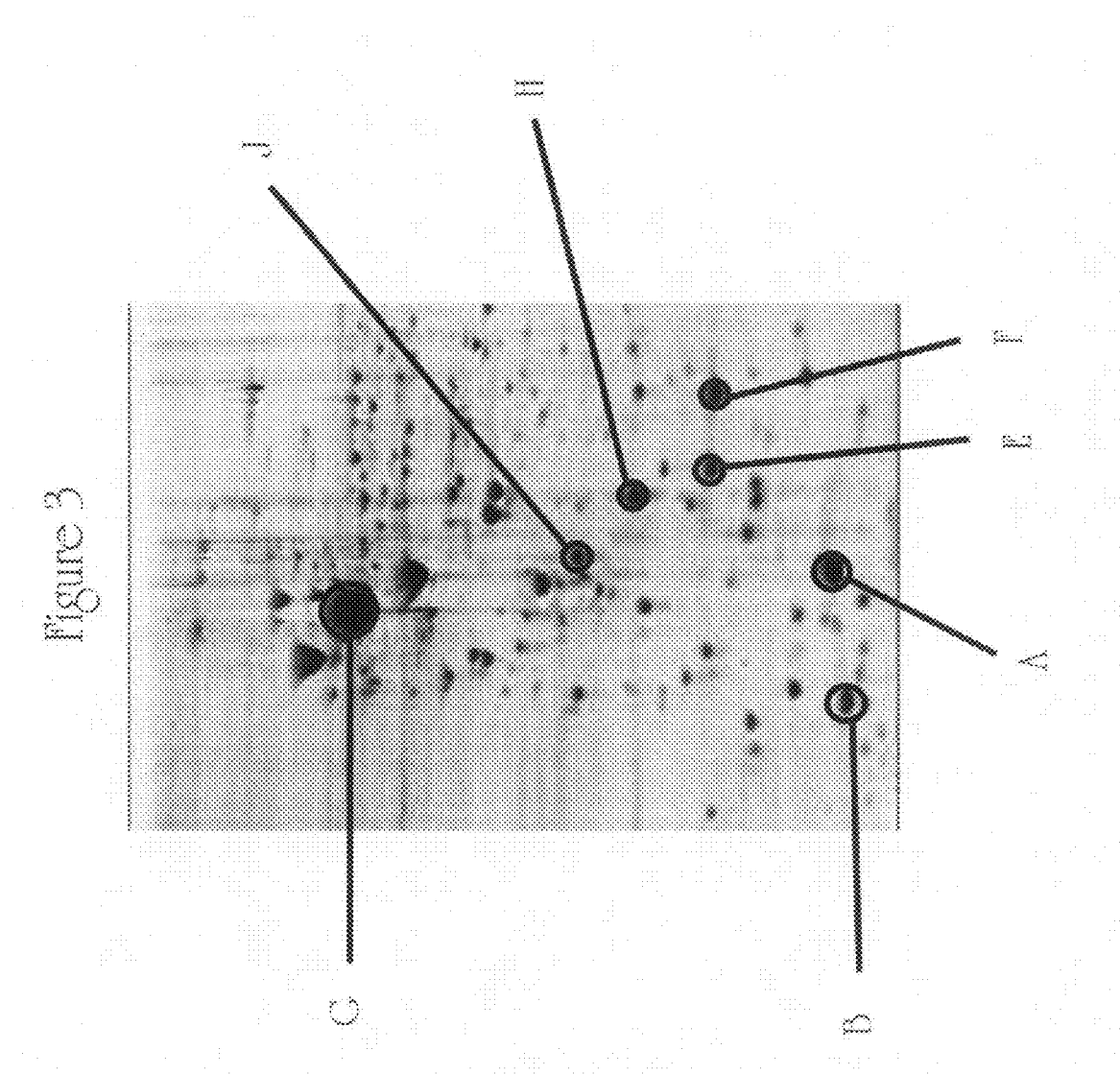
FIG. 3 illustrates the localization of *Bartonella henselae* proteins selected for further analysis. Coomassie-Blue stained two-dimensional SDS-PAGE gel with spots yielding greater than 63% reactivity to patient sera are circled and given an arbitrary letter designation for future reference.

Analysis of fourteen patient (*Bartonella henselae* IFA-positive) sera revealed reactivity to many *Bartonella henselae* proteins (FIG. 2A). In contrast, the seven normal (*Bartonella henselae* IFA-negative) sera tested demonstrated minimal reactivity to *Bartonella henselae* spots (FIG. 2B). Surprisingly, comparison of spot reactivities by PDQuest™ between all patient sera tested demonstrated no common protein reactivity between all samples. However, at least seven spots demonstrated reactivity to greater than 64% of the patient sera tested (FIG. 3 and Table 2). These spots reacted to 0-14% of the normal sera tested (Table 2).

TABLE 2

Reactivity of patient (*Bartonella henselae* IFA positive) and normal (*Bartonella henselae* IFA negative) sera to noted spots.

| Spot Designation | Patient Sera (% reactivity) | Normal Sera (% reactivity) |
|------------------|-----------------------------|----------------------------|
| A | 10/14 (71%) | 1/7 (14%) |
| B | 12/14 (86%) | 1/7 (14%) |
| E | 9/14 (64%) | 0/7 (0%) |
| F | 9/14 (64%) | 0/7 (0%) |
| G | 9/14 (64%) | 0/7 (0%) |
| H | 10/14 (71%) | 1/7 (14%) |
| J | 9/14 (64%) | 1/7 (14%) |

EXAMPLE 3

Identification of Reactive Spots

Protein spots were excised from a Coomassie-Blue stained gel, and subjected to trypsin digestion and identification by MALDI-MS. Comparison of the molecular weights of the resultant trypsin fragments to the expected molecular weights of the digestion products from the *Bartonella henselae* genome sequence revealed the identities of these proteins (Table 3). Spot A was identified as GroES, a chaperonin. Spot B was identified as RpIL, the L7/L12 segment of the 50S ribosome subunit. Spots E and F were identified as BepA, which has an unknown function. Spot G was identified as GroEL, a heat shock protein. Spot H was identified as SodB, a superoxide dismutase, and also was identified as UbiG, a chaperonin and a heat shock protein. Spot J was identified as the ABC transporter.

TABLE 3

Properties of identified proteins.

| Spot Designation | Protein | Accession No. | MW (kDa) | pI | Gene Size (bp) | Putative Function | SEQ ID NO: |
|---|---|---|---|---|---|---|---|
| A | GroES | 49476035 | 10.7 | 5.23 | 297 | chaperonin | 11 |
| B | RplL | 49475397 | 12.7 | 4.61 | 369 | 50S ribosomal protein L7/L12 | 12 |
| E, F | BepA | 49476039 | 19.7 | 6.15 | 525 | unknown | 13 |
| G | GroEL | 6226790 | 57.6 | 4.91 | 1644 | chaperonin, heat shock protein | 14 |
| H | SodB | 49475260 | 23.1 | 5.75 | 600 | superoxide dismutase | 15 |
| H | UbiG | 49475201 | 28 | 7.35 | 741 | 3-dimethyl ubiquinone-93-methyltransferase | 16 |
| J | ABC transporter | 49475425 | 28.2 | 5.41 | 750 | periplasmic amino acid-binding protein | 17 |

Figure 4:
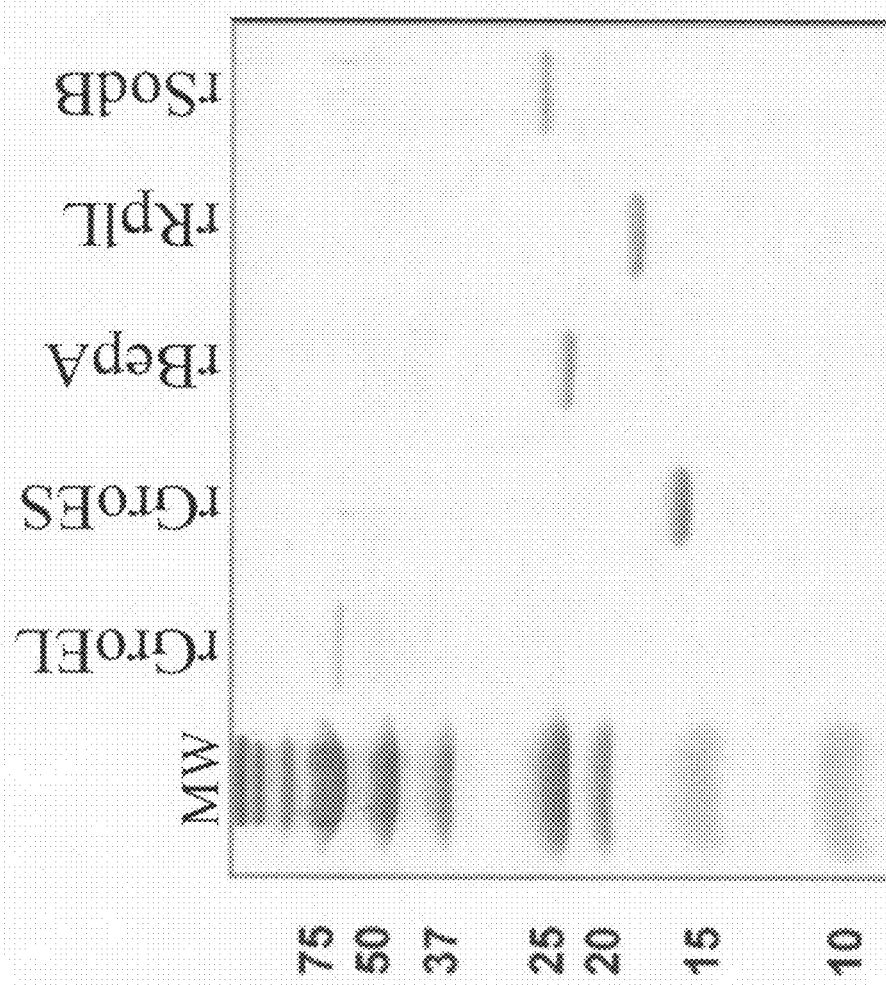
FIG. 4 illustrates a Coomassie-Blue stained gel of purified recombinant proteins. One µg of each of recombinant GroEL, recombinant GroES, recombinant BepA, recombinant RpIL, and recombinant SodB were run on a 15% SDS-PAGE gel and stained with Coomassie Blue to demonstrate purity of these recombinant proteins. In the figure, the symbol "r" stands for the word "recombinant."

The amino acid sequence of each of the GroES, RpIL, BepA, GroEL, SodB, UbiG, and the ABC transporter proteins was previously published (see Table 3 for the respective accession numbers). The gene encoding each of the GroEL, GroES, BepA, RpIL, and SodB proteins was cloned and expressed with an N-terminal histidine tag that allowed for purification over an $Ni^{2+}$ column. After purification, protein fractions were run on an SDS-PAGE gel which revealed an estimated purity of greater than 90% for each protein isolated (FIG. 4).

EXAMPLE 4

**Western Analysis of Patient Sera to Select *Bartonella henselae* Proteins**

Figure 5:
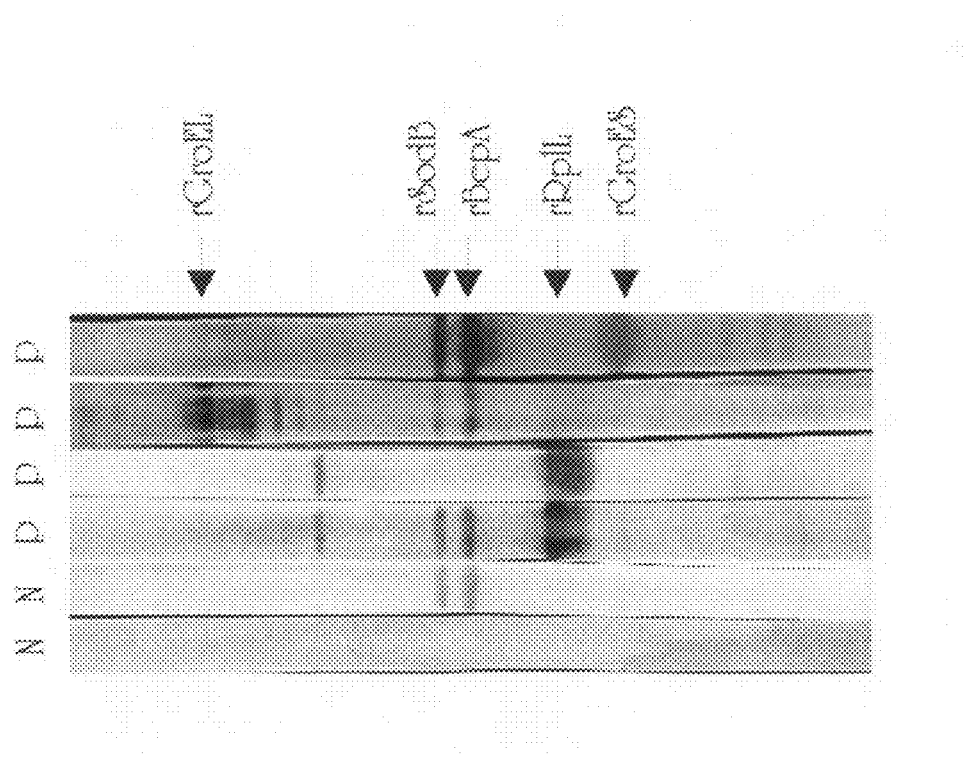
FIG. 5 illustrates serum IgG reactivity to recombinant GroEL, recombinant SodB, recombinant BepA, recombinant RpIL, and recombinant GroES. These proteins were mixed in equal concentrations, and loaded into each lane of a 15% SDS-PAGE gel. After transfer, membranes were exposed to either patient sera (P) or normal sera (N). Bound antibodies were detected with anti-human IgG-horse-radish peroxidase ("HRP"). Blots shown are representative. In the figure, the symbol "r" stands for the word "recombinant."

Western analysis of two-dimensional gels revealed the overall reactivity of patient sera to *Bartonella henselae* suggesting five proteins for further study (GroES, GroEL, SodB, RpIL, and BepA). In order to determine the reactivity of sera to these proteins, recombinant GroES, recombinant GroEL, recombinant SodB, recombinant RpIL, and recombinant BepA were simultaneously separated by one-dimensional SDS-PAGE gels and subsequently electrophoretically transferred to PVDF membranes. Individual lanes containing all of the chosen proteins were screened with either patient or normal sera (FIG. 5). Patient sera demonstrated reactivity to all proteins in various combinations. However, normal serum demonstrated recognition of recombinant SodB and recombinant BepA. Recombinant SodB and recombinant BepA were not analyzed further due to this reactivity.

Figure 6:
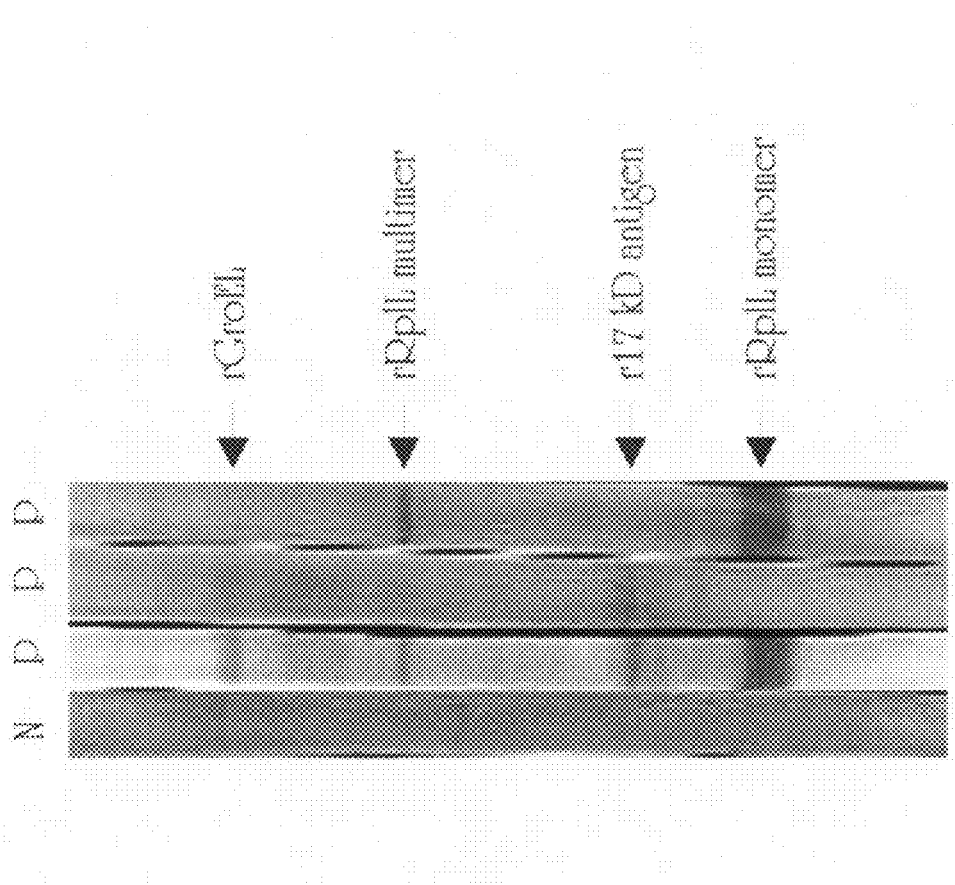
FIG. 6 illustrates human serum IgG reactivity to recombinant GroEL, recombinant RpIL, and recombinant 17 kDa antigen. Recombinant GroEL, recombinant RpIL, and recombinant 17 kDa antigen were mixed in equal concentrations, and loaded into each lane of a 15% SDS-PAGE gel. After transfer, membranes were exposed to either patient sera (P) or normal sera (N). Bound antibodies were detected with anti-human IgG-HRP. Blots shown are representative. In the figure, the symbol "r" stands for the word "recombinant."

A subsequent Western blot was produced that combined recombinant GroEL, recombinant RpIL, and the recombinant 17 kDa protein. The 17 kDa protein has been previously used in an ELISA to determine if patients have an antibody response to *Bartonella henselae*; although normal sera did not demonstrate greater than background reactivity to the 17 kDa protein, not all patient sera contain antibodies to this protein (Loa, C. C., E. Mordechai, R. C. Tilton, and M. E. 2006. Adelson. Production of recombinant *Bartonella henselae* 17 kDa protein for antibody-capture ELISA. Diagnostic Microbiology and Infectious Disease. In Press). Utilization of recombinant GroEL, recombinant RpIL and recombinant 17 kDa protein in combination resulted in recognition of at least one band by twenty-four of twenty-eight patient sera and seven of twenty-one normal sera (FIG. 6). Thus, this Western blot has a sensitivity of 85.7% and a specificity of 66.7%.

EXAMPLE 5

Proteolytic and Chemical Digestion of RpIL

In an effort to localize the immunodominant and cross-reactive regions of RpIL and impart increased specificity to the Western blot assay, digestions of recombinant RpIL were performed. Recombinant RpIL (18 μg) was digested with 29 μg 3-bromo-2-(2-nitrophenylsulfenyl)skatol ("BNPS-skatol") (MP Biomedicals, Irvine, Calif.) in 100% acetic acid overnight at 47° C. The reaction was stopped by the addition of 24 μl of $ddH_2O$. Recombinant RpIL (55 μg) was incubated with 1 μg endoproteinase Arg-C (Calbiochem, San Diego, Calif.), activation solution (5 mM DTT, 0.5 mM EDTA) and incubation solution (0.1 M Tris HCl, 0.01 M $CaCl_2$). The reaction was incubated overnight at 37° C.

Based on sequence analysis, chemical digestion with BNPS-skatol cleaves recombinant RpIL at one site (after the amino acid residue at position 73) resulting in fragments of approximately 8200 and 9400 Da in size. Proteolytic digestion with endoproteinase Arg-C results in cleavage at three sites (after the amino acid residues at positions 14, 28, and 119) resulting in fragments of approximately 1700, 1500, 9500, and 4900 Da in size. Recombinant RpIL was digested using these two methods, which resulted in fragments of the appropriate size (data not shown). Subsequent Western analysis was performed utilizing patient and normal human sera (FIG. 7). Cleavage with BNPS-skatol did not provide any additional evidence for the localization of epitopes. However, patient sera appeared to bind most frequently to an approximately 10 kDa fragment that resulted from endoproteinase Arg-C digestion of rRpIL (see SEQ ID NO:18 for the amino acid sequence of this 10 kDa fragment). Ten of eleven patient sera bound to a 10 kDa digestion product, while three of twelve normal sera bound.

EXAMPLE 6

ELISA Analysis

In order to provide a semi-quantitative result, ELISAs using recombinant proteins as the solid phase were developed. Purified proteins diluted in coating buffer (0.015 M Na₂CO₃, 0.035 M NaHCO₃ (pH 9.6)) were used to coat 96-well Immulon 2 high-binding plates (DYNEX Technologies, Chantilly, Va.). Recombinant GroES, recombinant GroEL, recombinant RpIL, and recombinant BepA were used at 0.25, 0.25, 0.01, and 2 μg/ml, respectively, to coat plates. After overnight incubation at 4° C., the plates were washed with PBS-Tween 20, blocked with 1% BSA for one hour at 37° C., and washed again. Dilutions of serum in 1% bovine serum albumin were added and then incubated for one hour at 37° C. Antigen-specific antibodies were detected by goat anti-human IgG-HRP (KPL, Gaithersburg, Md.) and developed with 3,3',5,5'-tetramethylbenzidine ("TMB") (Moss, Pasadena, Md.) for fifteen minutes. The reaction was stopped with 1N HCl and the absorbance at 450 nm was recorded after a standardized period of ten minutes.

An ELISA using recombinant RpIL as the coating antigen demonstrated reactivity to fourteen of eighteen patient sera and seven of seventeen normal sera. This ELISA exhibited a sensitivity of 78% and a specificity of 59% (Table 4). Sixteen of twenty patient sera and fourteen of twenty normal sera demonstrated reactivity by recombinant GroEL ELISA. Recombinant GroES ELISA demonstrated reactivity with sixteen of twenty patient sera and seventeen of twenty normal sera. An ELISA using recombinant BepA as the coating antigen demonstrated reactivity to twelve of fourteen patient sera and five of nine normal sera. Sensitivities and specificities of ELISAs based on these proteins were determined (Table 4).

TABLE 4

Sensitivities and specificities of ELISAs using various recombinant proteins as coating antigens.

| Recombinant Protein | Sensitivity (%) | Specificity (%) |
| --- | --- | --- |
| recombinant GroES | 80 | 15 |
| recombinant RpIL | 78 | 59 |
| recombinant BepA | 86 | 44 |
| recombinant GroEL | 80 | 30 |

We claim:

1. A method for determining whether a subject contains an antibody in sera against an antigen, wherein said antigen is a combination of separated GroES, GroEL, and RpIL proteins having an amino acid sequence set forth in SEQ ID NOS: 11, 12, and 14 respectively, comprising the steps of:

(a) providing an antigen, wherein said antigen is a combination of separated GroES, GroEL, and RpIL proteins having an amino acid sequence set forth in SEQ ID NOS: 11, 12 and 14 respectively;

(b) providing a sample from a subject;

(c) conducting an immunoassay on said sample utilizing said antigen, wherein said immunoassay detects the presence of antibodies that recognize said combination of GroES, GroEL and RpIL; and (d) determining that the subject contains an antibody against said antigen if the results of the immunoassay indicate that an antibody that recognizes said antigen is present in said sample.

2. The method of claim 1, wherein the subject is a human.

3. The method of claim 1, wherein the immunoassay is an immunofluorescence assay (IFA).

4. The method of claim 1, wherein the immunoassay is an enzyme-linked immunosorbent assay (ELISA).

5. The method of claim 1, wherein the immunoassay is a Western blot.

6. The method of claim 1, wherein the antigen is an isolated recombinant antigen.

7. The method of claim 1, wherein said antigen further comprises BepA and SodB.

8. A method for determining whether a subject contains an antibody in sera against *Bartonella henselae*, comprising the steps of:

(a) providing an isolated antigen, wherein said antigen is a combination of separated GroES, GroEL, and RpIL proteins having an amino acid sequence set forth in SEQ ID NOS: 11, 12, and 14 respectively;
(b) providing a sample from a subject;
(c) conducting an immunoassay on said sample utilizing said antigen, wherein said immunoassay detects the presence of antibodies that recognize said combination of GroES, GroEL, and RpIL antigen; and
(d) determining that the subject contains an antibody against said antigen if the results of the immunoassay indicate that an antibody that recognizes said antigen is present in said sample.

9. The method of claim 8, wherein the subject is a human.

10. The method of claim 8, wherein the immunoassay is an immunofluorescence assay (IFA).

11. The method of claim 8, wherein the immunoassay is an enzyme-linked immunosorbent assay (ELISA).

12. The method of claim 8, wherein the immunoassay is a Western blot.

13. The method of claim 8, wherein the antigen is an isolated recombinant antigen.

14. The method of claim 8, wherein said antigen further comprises BepA and SodB.

15. A kit, comprising:
an isolated antigen wherein said antigen is a combination of separated GroES, GroEL, and RpIL proteins having an amino acid sequence set forth in SEQ ID NOS: 11, 12 and 14 respectively; and
reagents necessary for conducting an immunoassay, wherein the immunoassay is capable of detecting the presence of an antibody in a sample, and wherein the antibody is capable of binding to said antigen.

16. The kit of claim 15, wherein the immunoassay is an immunofluorescence assay (IFA).

17. The kit of claim 15, wherein the immunoassay is an enzyme-linked immunosorbent assay (ELISA).

18. The kit of claim 15, wherein the immunoassay is a Western blot.

19. The kit of claim 15, wherein the isolated antigen is an isolated recombinant antigen.

20. The kit of claim 15, wherein said antigen further comprises BepA and SodB.

21. A method for determining whether a subject contains an antibody in sera against *Bartonella henselae*, comprising the steps of:
(a) providing an isolated antigen, wherein said antigen is a combination of separated GroEL, RpIL, and 17 kDa protein from *Bartonella henselae*;
(b) providing a sample from a subject;
(c) conducting an immunoassay on said sample utilizing said antigen, wherein said immunoassay detects the presence of antibodies that recognize said combination of GroEL, RpIL, and 17 kDa protein; and
(d) determining that said subject contains an antibody in sera against *Bartonella henselae* if the result of the immunoassay indicates that an antibody that recognizes said antigen is present in said sample.

22. The method of claim 21, wherein the subject is a human.

23. The method of claim 21, wherein the immunoassay is an immunofluorescence assay (IFA).

24. The method of claim 21, wherein the immunoassay is an enzyme-linked immunosorbent assay (ELISA).

25. The method of claim 21, wherein the immunoassay is a Western blot.

26. The method of claim 21, wherein the isolated antigen is an isolated recombinant antigen.

* * * * *